(12) United States Patent
Drezet et al.

(10) Patent No.: US 7,501,635 B2
(45) Date of Patent: Mar. 10, 2009

(54) TOMOGRAPH COMPRISING DETECTORS HAVING A SPECIFIC SHAPE

(75) Inventors: Arnaud Drezet, Grenoble (FR); Olivier Monnet, Tullins (FR); Guillaume Montemont, Grenoble (FR); Loick Verger, Grenoble (FR)

(73) Assignee: Commissariat a l'Energie Atomique, Paris (FR)

( * ) Notice: Subject to any disclaimer, the term of this patent is extended or adjusted under 35 U.S.C. 154(b) by 163 days.

(21) Appl. No.: 11/630,682

(22) PCT Filed: Jun. 27, 2005

(86) PCT No.: PCT/FR2005/050499

§ 371 (c)(1),
(2), (4) Date: Dec. 27, 2006

(87) PCT Pub. No.: WO2006/008409

PCT Pub. Date: Jan. 26, 2006

(65) Prior Publication Data

US 2008/0042069 A1    Feb. 21, 2008

(30) Foreign Application Priority Data

Jun. 28, 2004    (FR) .................................. 04 51350

(51) Int. Cl.
*H01L 27/146*    (2006.01)

(52) U.S. Cl. ............................ 250/370.09; 250/363.01; 250/363.02; 250/363.03; 250/363.04

(58) Field of Classification Search ............. 250/370.09, 250/363.03, 363.02, 363.01, 363.04
See application file for complete search history.

(56) References Cited

U.S. PATENT DOCUMENTS

| 6,229,870 B1 * | 5/2001 | Morgan .......................... 378/9 |
| 6,285,028 B1 | 9/2001 | Yamakawa |
| 6,399,951 B1 | 6/2002 | Paulus et al. |
| 6,891,166 B2 * | 5/2005 | Brahme et al. ............... 250/389 |

FOREIGN PATENT DOCUMENTS

| EP | 1 408 347 A1 | 4/2004 |
| EP | 1 413 898 A1 | 4/2004 |

OTHER PUBLICATIONS

Wai-Hoi Wong, "Designing a Stratified Detection System for PET Cameras", IEEE Transactions on Nuclear Science, vol. 33, No. 1, Feb. 1986, pp. 591-596.

* cited by examiner

*Primary Examiner*—Christine Sung
(74) *Attorney, Agent, or Firm*—Oblon, Spivak, McClelland, Maier & Neustadt, P.C.

(57) ABSTRACT

A tomograph type detection device including a plurality of detection elements arranged in a form of a ring and electrodes on each face of the elements. Each electrode includes a connector, all the connectors being located on the external periphery of the ring of detection elements.

19 Claims, 5 Drawing Sheets

TOMOGRAPH COMPRISING DETECTORS HAVING A SPECIFIC SHAPE

TECHNICAL DOMAIN AND PRIOR ART

The invention relates to the domain of medical imagery by positron emission tomography (PET) and more specifically the development of a PET imagery system dedicated to small animals (principally rodents) so as to improve the spatial resolution.

Most PET systems use rectangular parallelepiped shaped scintillator detectors 2 assembled in rings as illustrated in FIG. 1, around an object 4 to be imaged.

The object 4 to be imaged actually behaves like a gamma radiation source, output from disintegration of a radiotracer previously injected into the object. These gamma rays are emitted in pairs, at 180° from each other and are therefore detected by two coincident detectors.

These systems were developed for studies related to the human body, and are unsuitable for imagery of rodents. The inside diameter r2 of the detection ring is very much reduced so as to adapt to the anatomical dimensions of the small animal. This large reduction in diameter brings about a serious degradation of the spatial resolution: there is a degradation in positioning due to penetration of radiation through the edge of the detector, called the parallax error as illustrated on FIG. 2.

On this figure, references 6, 8 denote a real trajectory and a reconstituted trajectory respectively, the difference between them creating the so-called parallax error.

This phenomenon only becomes a real problem in cases in which the diameter of the object to be imaged is approximately the same as the diameter of the imagery system, which is the case for rodents. In this case the front faces 10 of the detectors have to be used as the starting point for reconstitution of the trajectories of incident gamma rays (FIG. 2).

Some inventors have developed detectors formed from several different crystals to overcome this difficulty (see the article by W. H. Wong, "Designing a stratified detection system for PET cameras", IEEE Transaction on Nuclear Science, 1986, 33(1): p.591-596). The generated signal is different depending on the material in which the interaction takes place. This provides a means of positioning the interaction location.

Nevertheless, these systems called "phoswich", are complex to implement electronically for a moderate gain in spatial resolution.

The use of a semiconducting material can prevent this difficulty. In such a detector, the generated signal is a set of electrical charges that are guided in the detector by the electric field applied to it. Their migration in the detector under the influence of the electrical field causes an induction of charges at the electrodes of the detector. The objective is to position the induction zone on these electrodes as precisely as possible. This can be done by geometrically varying the shape of the electrodes by breaking them down into segments.

The most frequently used segmented electrodes structure consists of a checkerboard patterned anode (or cathode) with side dimension n, namely $n^2$ segments (or "strips") as illustrated on FIG. 3, and a full face cathode (or anode). These $n^2$ segments are connected to the same number of electronic processing channels 12, 14. For a fine segmentation as is required to image a small animal, this requires a very high electronic density. In practice, the cost and management complexity of electronic channels for this structure are prohibitive for PET imagery of small animals.

Structures are available for simplifying information processing, so as to reduce these $n^2$ electronic channels on the anode (or cathode) to 2n channels as illustrated on FIG. 4. The electronics is simplified, but the installation of the connections is difficult to achieve because the final system is composed of several detectors stacked on each other.

One solution to this problem among existing structures is to implement segmentation both on the anode and the cathode as illustrated on FIG. 5.

There are always 2n anode and cathode segments arranged perpendicularly. In the context of a PET application to small animals, this arrangement suffers from two disadvantages.

In a complete PET system, several base structures 20, 22 (FIG. 6) carrying the segmented electrodes have to be arranged adjacent to each other to form the detection ring. With a structure of electrodes intersecting each other perpendicularly, the connections 23 of a family of electrodes (anode or cathode) are necessarily made inside the ring. This creates a serious difficulty for assembly, and lost detection space.

The diagram in FIG. 6 illustrates this problem. It shows two consecutive "stripped" detectors 20, 22 making up a complete detection ring 24. Note the size problem that occurs, particularly between the horizontal electronic channels 25 output from the detector 20 and the detector 22, the detector 20 in turn being hindered by connections of the detector located on the other side, not shown on the figure.

Furthermore, the total number of channels in such a system remains high despite the gain achieved by changing from $n^2$ channels to 2n channels.

Therefore the problem of the connection size and a problem due to the number of channels arise.

PRESENTATION OF THE INVENTION

In order to solve the problem of degradation of the spatial resolution while exceeding the limits encountered by systems developed so far, this invention proposes a specific geometric arrangement of the electrodes.

The invention can give a very good spatial resolution for a minimum electronic cost.

To prevent connection wires from being present in the detection zone, the invention proposes to present all anode and cathode outputs on the external periphery of the detectors ring.

Therefore, the invention relates to a tomograph type detection device comprising a plurality of detection elements arranged in the form of a ring, electrodes on each face of these elements, each electrode being provided with connection means, all these connection means being located on the external periphery of said ring of detection elements.

The electrodes may be in the form of segments, all segments covering a face of a detection element being arranged along a direction inclined from the assembly of segments covering the other face of said detection element.

The ring may have an inside periphery approximately in the form of a circle, an external periphery approximately in the form of a circle, these two circles being concentric, the segments being inclined with respect to a radius of the external periphery, with an angle smaller than the angle delimited by said radius and a tangent (T1, T2) to the internal circle that meets said radius at the intersection point of this radius on the outside circle.

The invention also relates to a tomograph type detection device characterised in that it comprises:
- a plurality of detection elements arranged in the form of a ring, this ring having an inside periphery forming a circle, an outside periphery forming a circle, these two circles being concentric,
- electrodes on each face of these detection elements, the electrodes on one face being inclined with respect to a radius of the outside periphery, with an angle less than the angle delimited by said radius and a tangent to the inside circle that meets said radius at the intersection point of this radius on the outside circle.

Each electrode may also be provided with connection means, all of these connection means being located on the outside periphery of said ring of detection elements.

Therefore according to the invention, it is proposed to arrange the electrodes so as to bring all the connections to a single side of the detector, which is the outside of a detection ring.

In a device according to the invention, at least part of the segments can cover at least two detectors or each electrode may be common to at least two detection elements, for example between one and 20 detectors.

Therefore some bands or some segments can be extended on adjacent detectors: the number of connections per detector is thus reduced.

For example, the electrodes may be inclined on each face by an angle less than $\beta 1$ or $\beta 2$ from a radial axis passing through the central axis of the system and the edge of each detector located in a plane perpendicular to this central axis, where $\beta 1$ and $\beta 2$ are defined as being the angle between an outside radius of the device and a corresponding tangent to the inside circumference of the device.

For example $\beta 1 = \beta 2 \approx 52.5°$.

Electrodes on each face of the detection elements may be arranged in the form of fans defining two crossed fans.

Detection elements are preferably made of a semiconducting material, for example CdZnTe, or CdTe, or GaAs or Ge or HgI2 or Si.

The inside radius of the ring of detectors may for example be between 15 mm and 100 mm, and its outside radius may be between 35 mm and 400 mm.

The invention can be used to make a tomograph type device with simplified connections. Such a device is particularly suitable for work on small animals such as rodents.

DETAILED PRESENTATION OF PARTICULAR EMBODIMENTS

Figure 7A:
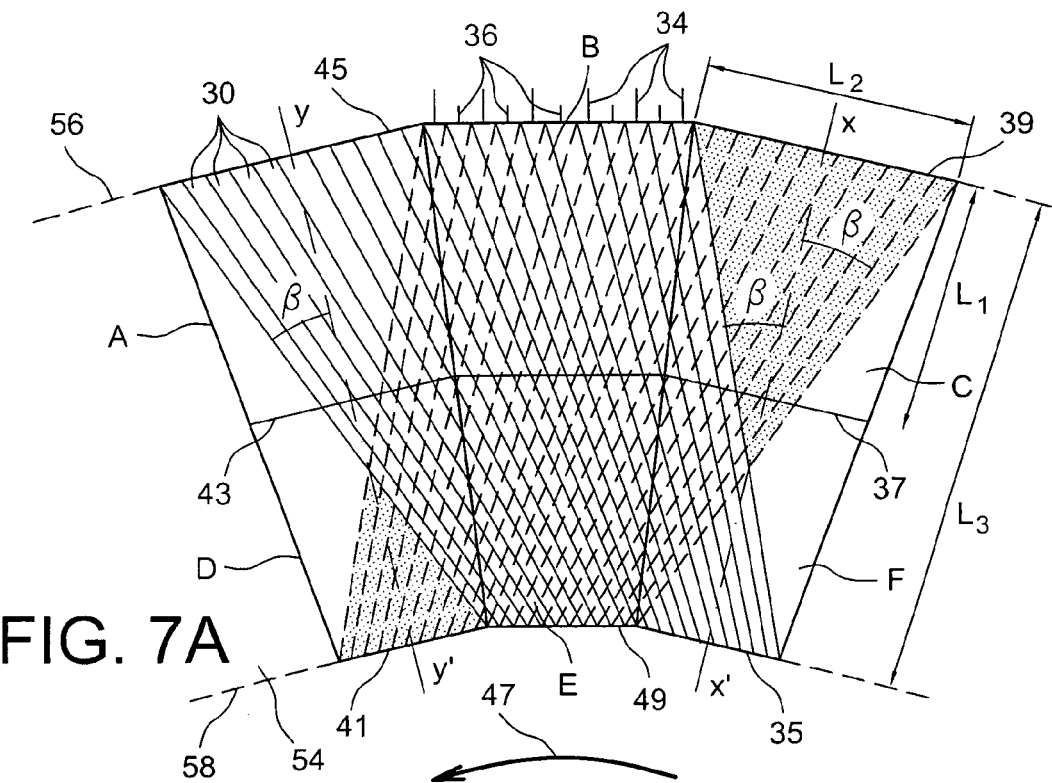
FIGS. 7A, 7B, 8 describe a device according to the invention.
Figure 7B:
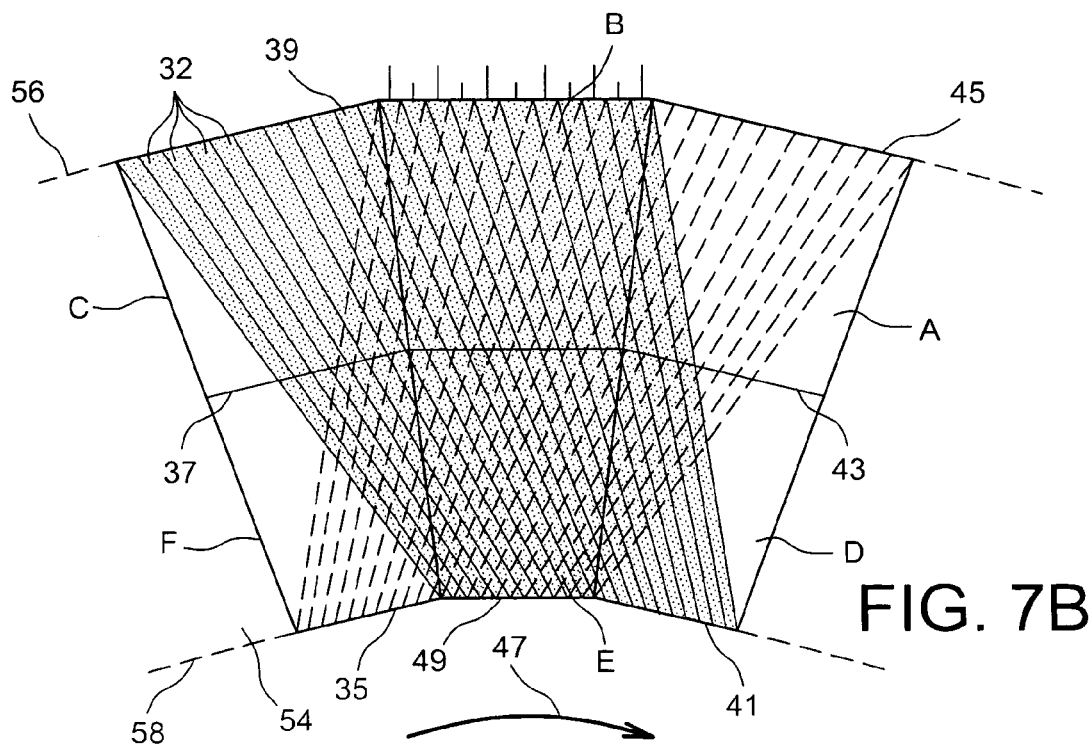

One example of a detection device according to the invention is illustrated on FIGS. 7A and 7B, FIG. 7A representing the front face of a set of detector blocks A-F (for example the cathode side) and FIG. 7B the back face of this same assembly (for example the anode side).

Detection elements A, B, C, D, E, F, are represented by trapeziums. On these FIGS. 7A and 7B, these detection elements form an angular portion of a detection ring 54 shown in dashed line 56, 58 showing the ring outside and inside dimensions respectively. Each of these inside and outside peripheries is approximately circular. This ring 54 is extended laterally by other detection elements not shown.

References 30 and 32 denote electrodes that contribute to the detection of interactions that take place in these detection elements.

Globally, these electrodes 30, 32 are segmented in the form of crossed fans, the electrodes located on one face of the detectors being oriented along one direction relative to the path of the ring of detectors in a specific direction (anticlockwise direction identified by arrow 47 on FIG. 7A), and the electrodes located on the other face being oriented in the other direction along this same path.

Figure 1:
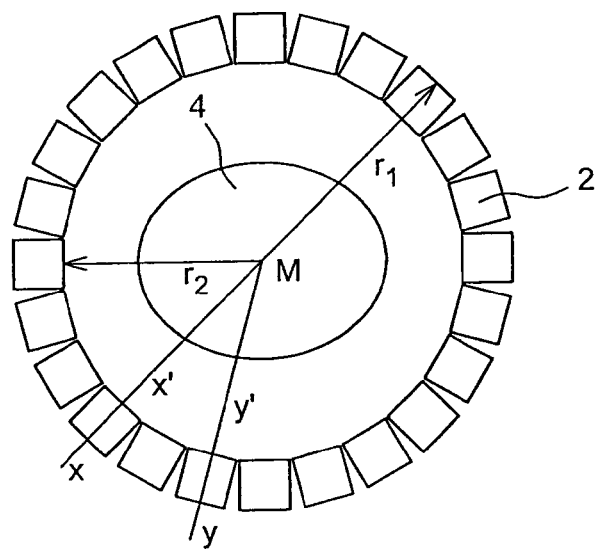
FIGS. 1-6 describe devices according to prior art.
Figure 2:
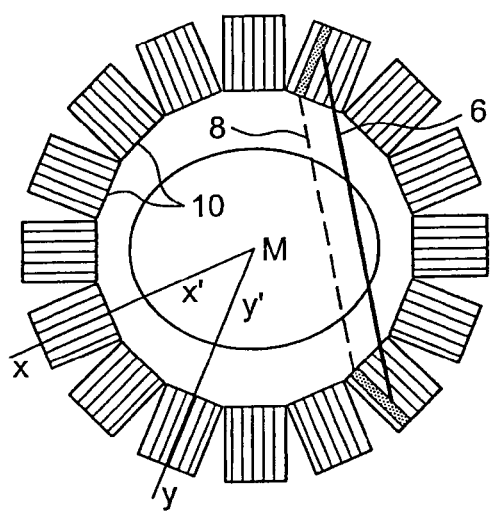
Figure 3:
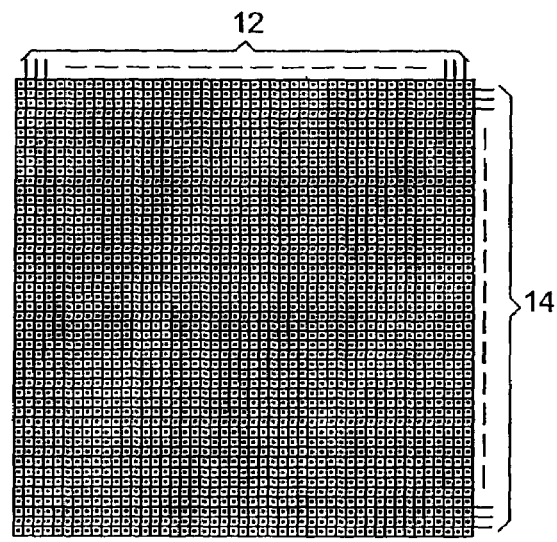
Figure 4:
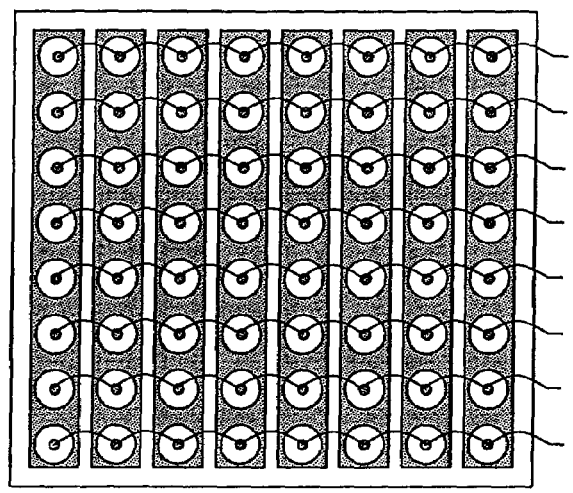
Figure 5:
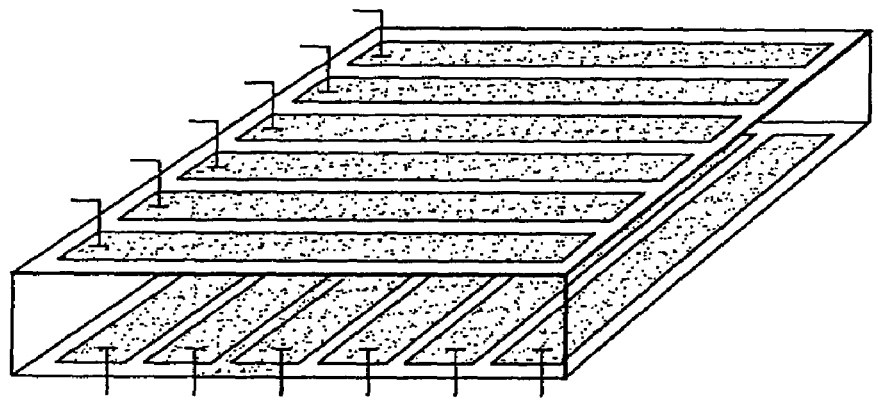

Therefore, the electrodes are inclined by an angle of inclination $\beta$ or $-\beta$ from a radial axis XX' or YY' that passes through the central axis of the system and approximately through the middle of the edge 35, 37, 39, 41, 43, 45 of each detector also as shown on FIG. 1. These axes XX', YY' are actually in a plane perpendicular to the central axis of the system; this central axis, shown on FIGS. 1 and 2, is perpendicular to the plane of these figures and is shown symbolically by the point M.

References 34 and 36 denote connections used to sample a signal on each electrode.

The figure only shows connections output from the detection element B, but there are similar connections output from elements A, C adjacent to B, also on the outside 56 of the ring 54.

It is clear that these connections are all located on the outside 56 of this ring of detectors, this side being defined particularly by the edges 39, 45.

In this example, it can be seen that each electrode or almost each electrode (inclined electrodes are possible but some are only distributed on a single detector) runs on the surface of at least two or even more than two detectors.

FIGS. 7A and 7B show two rows of detectors (A, B, C for the first row, D, E, F for the second row). On this example, each electrode is present simultaneously on three detector blocks.

If the device only comprises one row (for example A, B, C), some electrodes would be present on two detectors and others would only be present on one detector despite their inclination.

The number of blocks passed through depends on the inside and outside radii of the ring 54 of detectors in the system, the size of the detector blocks and the inclination $\beta$ of the electrodes.

Figure 8:
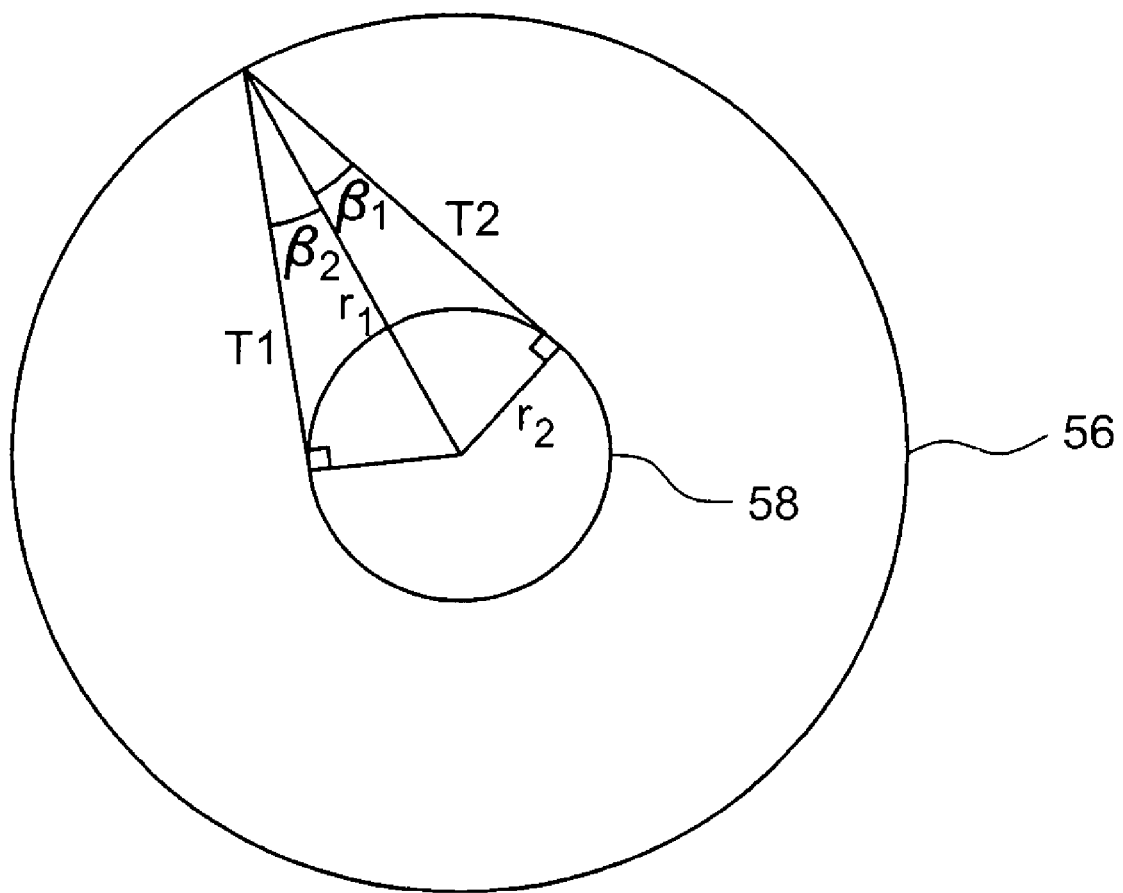

Thus, a PET system for small animals has an inside radius r2 that can vary from 25 mm to 75 mm, the outside radius r1 of the ring depending on the thickness (indicated by L3 on FIG. 7A) of the detector material (for example, radii r1 and r2 are measured as shown on FIG. 1 or FIG. 8). This thickness for a semiconductor such as CdZnTe is between 20 mm and 100 mm to achieve a radiation stopping power equal to 65% to 99%, which gives an outside radius varying from 45 mm to 175 mm.

The values of the angle of inclination $\beta$ of the cathodes are limited by two tangents (T1 and T2) to the inside circumference 58 of the system as illustrated on FIG. 8.

The electrodes on one face are inclined from a radius of the outside periphery 56 by an angle $\beta 1$, $\beta 2$ less than the angle delimited by said radius and a tangent T1, T2 to the inside circle 58 that meets said radius at the intersection point of this radius on the outside circle 56.

If this inclination is exceeded, the electrodes on a same face then open up on the outside of the ring such that the other electrodes cannot have the same configuration. The system in which $\beta 1 < \beta < 90°$ is also possible.

In the above example, the maximum angle of inclination is obtained for a large inside radius r2 (75 mm) and the smallest associated outside radius r1 (95 mm), namely:

$$\beta1=\beta2=\beta=\text{asin}(75/95)\approx 52.5°$$

The angle of inclination of the anodes is limited by the same values.

Eventually, the two families of electrodes may be inclined at an angle β, β' between 0 and β1 and β2 respectively (−52.5° and 52.5° respectively in the above example). β and β' are not necessarily equal.

For mechanical strength reasons, the sides (L1 and/or L2 (see FIG. 7A)) of the detector blocks are preferably between 5 mm and 30 mm long for CdZnTe.

Table I below contains values of β1 and β2 for various materials and various geometrical configurations.

TABLE I

|  |  | L3 (mm) | R1 (mm) | R2 (mm) | β1 = β2 |
|---|---|---|---|---|---|
| Si | Min | 40 | 55 | 15 | 45.6° |
|  | Max | 270 | 370 | 100 |  |
| Ge | Min | 20 | 35 | 15 | 56.4° |
|  | Max | 130 | 230 | 100 |  |
| GeAs | Min | 20 | 35 | 15 | 56.4° |
|  | Max | 130 | 230 | 100 |  |
| CdTe:Cl | Min | 20 | 35 | 15 | 56.4° |
|  | Max | 100 | 200 | 100 |  |
| CdZnTe | Min | 20 | 35 | 15 | 56.4° |
|  | Max | 100 | 200 | 100 |  |
| HgI$_2$ | Min | 10 | 25 | 15 | 65.4° |
|  | Max | 70 | 100 | 100 |  |

L1 will depend on L3 (see FIG. 7A) and the number of superposed rings (for example two rings ABC and DEF are superposed on FIG. 7A). For example, L2. will be equal to 270 mm in the first case (Si), 100 mm in the second case (Ge), 130 mm in the third case (130 mm), 30 mm in the fourth case (CdTe:Cl) and in the fifth case (CdZnTe), and 70 mm in the latter case (HgI2).

The number of blocks through which a segment or electrode passes varies depending on the selected dimensions and the angle β.

For a ring with a detection thickness L3=20 mm, composed of 20 mm blocks (=L1) with an angle of inclination β of approximately 0°, some tracks or electrodes will only be present on a single detector.

On the other hand, for a 100 mm thick ring composed of twenty 5 mm blocks, electrodes may be present on 20 detectors.

Therefore each electrode may be present on 1 to 20 detector blocks.

This simultaneous arrangement of electrodes on several detectors can limit the total number of required electronic read channels.

Each electrode is common to three blocks in the example on FIGS. 7A and 7B.

However, the electronic processing channels 34, 36 are present only on blocks A, B and C. Blocks D, E and F are actually only extensions of A, B and C (respectively), to provide an additional stopping power.

Consequently, each electrode is actually common to two effective detection blocks that are called AD (A+D), BE (B+E) and CF (C+F).

On FIG. 7A, 22 anodes (11 starting from the lower end 41 of block D and 11 starting from block E) and 22 different cathodes (11 starting from the lower end 49 of block E and 11 starting from block F) pass through the effective block BE.

However, as illustrated on FIG. 7A, only 50% of the surface areas covered by the anode and the cathode planes thus defined intercept on block BE.

Therefore the number of voxels subdividing this block is equal to:

$$(22\times 22)/2 = 242 \text{ voxels}$$

Therefore, $n^2/2$ voxels (in this case 242) can be read with only n electronic channels per effective detector block (in this case 22).

With a classical orthogonally intersecting electrode pattern $N^2$ voxels could be read with 2N electronic channels, namely 121 voxels with 22 channels (11 cathodes and 11 anodes).

Figure 6:
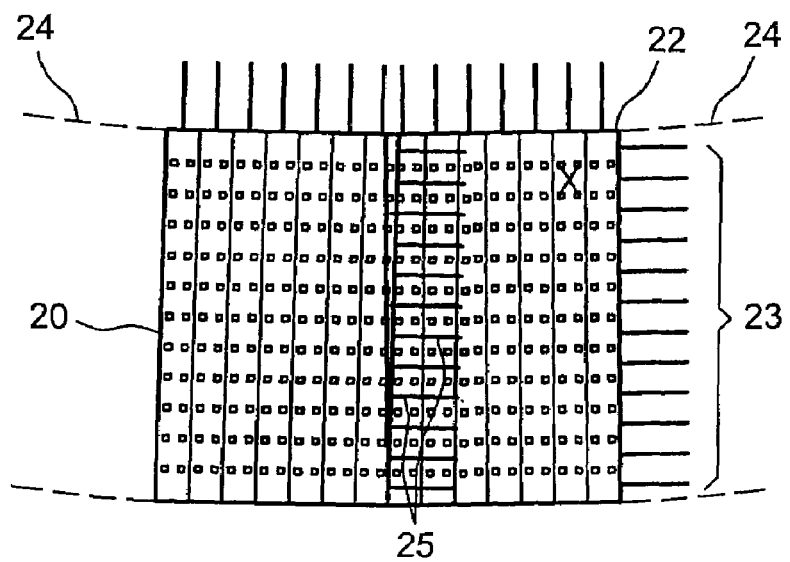

Therefore, in the example presented, the number of voxels observed for a single number of electronic channels is twice as many as are possible with the classical circuit shown in FIG. 6.

In the general case in which each electrode passes through I effective detection blocks with N anode channels and N cathode channels, the number of voxels subdividing a block is equal to:

$$(I\times N)\times(I\times N)/I = I\times N^2 \text{ voxels}$$

Therefore the gain is directly proportional to the number of electrodes put in common between the blocks.

Therefore, the invention can be used to set up connection means 34, 36 present on all of the ends of the tracks, but on a single face (the back face) of the detectors (on the side of the edges 39 and 45 of blocks A and C in FIG. 7A, or the side 56 of the ring 54).

This connection is easy to set up between the electrodes and the electronic processing systems or means, and furthermore does not reduce the space dedicated to detection.

The invention can also densify the segmentation of detectors, while strongly limiting the number of required electronic systems.

Furthermore, a detection module may be composed of a superposition of several rings like those described in FIGS. 7A, 7B, superposed perpendicularly to FIG. 7A, 7B to form a cylinder. For example, each detector may have an interelectrode distance less than or equal to 2 mm. It may be separated from detectors in another ring, for example, by a few tens of micrometers to enable insulation of the electrodes.

Electrodes are made on several detectors using the following steps.

The first step is to set up metallic contacts on detection blocks. These contacts are aligned between detectors that will form part of a single detection assembly, by a metrological check. The production technique is then the same as for conventional detectors.

The next step is to make a specific mask covering several detectors in a manner similar to what is done to make all types of detectors with metallic contacts, except for the angle of inclination β. Otherwise, the techniques used are currently used techniques.

A device according to the invention may be connected to usual means for processing signals taken from the electrodes in the usual manner, the number of measurement channels being adapted to the number of voxels to be measured.

The invention claimed is:

1. A tomograph type detection device, comprising:
 a plurality of detection elements, arranged in a form of a ring; and
 electrodes on a front face and a back face of the elements, forming an anode and a cathode, each electrode including a connector, all the connectors being located on the external periphery of the ring of detection elements, the electrodes being in a form of segments, all the segments covering a face of a detection element being arranged along a direction inclined from the assembly of segments covering the other face of the detection element.

2. A device according to claim 1, the ring having an inside periphery approximately in a form of a circle and an external periphery approximately in a form of a circle, the two circles being concentric, the segments being inclined with respect to a radius of the external periphery, with an angle smaller than the angle delimited by the radius and a tangent to the inside circle that meets the radius at the intersection point of the radius on the external circle.

3. A device according to claim 1, at least part of the electrodes covering at least two detection elements.

4. A device according to claim 1, at least part of the electrodes covering between one and 20 detection elements.

5. A device according to claim 1, the electrodes on the front face and the back face of the detection elements being arranged in a form of fans defining two crossed fans.

6. A device according to claim 1, the detection elements being made of a semiconducting material.

7. A device according to claim 6, the detection elements being made of CdZnTe, or CdTe, or GaAs, or Ge, or $HgI_2$, or Si.

8. A device according to claim 1, the inside radius of the ring of detection elements being between 15 mm and 100 mm.

9. A device according to claim 1, the outside radius of the ring of detection elements being between 35 mm and 400 mm.

10. A tomograph type detection device comprising:
a plurality of detection elements, arranged in a form of a ring, the ring having an inside periphery forming a circle and an outside periphery forming a circle, the two circles being concentric; and
electrodes on a front face and the back face of the detection elements, forming an anode and a cathode, the electrodes on one face being inclined with respect to a radius of the outside circle, with an angle less than the angle delimited by the radius and a tangent to the inside circle that meets the radius at the intersection point of the radius on the outside circle.

11. A device according to claim 10, each electrode including a connector, all of the connectors being located on the outside circle of the ring of detection elements.

12. A device according to claim 10, at least part of the electrodes covering at least two detection elements.

13. A device according to claim 10, at least part of the electrodes covering between one and 20 detection elements.

14. A device according to claim 10, the electrodes on the front face and the back face of the detection elements being arranged in a form of fans defining two crossed fans.

15. A device according to claim 10, the detection elements being made of a semiconducting material.

16. A device according to claim 15, the detection elements being made of CdZnTe, or CdTe, or GaAs, or Ge, or $HgI_2$, or Si.

17. A device according to claim 10, the inside radius of the ring of detection elements being between 15 mm and 100 mm.

18. A device according to claim 10, the outside radius of the ring of detection elements being between 35 mm and 400 mm.

19. A tomograph type detection device, comprising:
a plurality of detection elements, arranged in a form of a ring, the ring having an inside periphery approximately in a form of a circle, and an external periphery approximately in a form of a circle, the two circles being concentric; and
electrodes on the front face and the back face of the elements, forming an anode and a cathode, each electrode including a connector, all the connectors being located on the external periphery of the ring of detection elements, the electrodes being in a form of segments, all the segments covering a face of a detection element being arranged along a direction inclined from an assembly of segments covering the other face of the detection element, the segments being inclined with respect to a radius of the external circle, with an angle smaller than the angle delimited by the radius and a tangent to the inside circle that meets the radius at the intersection point of the radius on the external circle.

* * * * *